United States Patent [19]

Haber

[11] Patent Number: 4,908,022

[45] Date of Patent: Mar. 13, 1990

[54] DISPOSABLE SAFETY SYRINGE HAVING A RETRACTABLE NEEDLE CANNULA AND CANNULA LOCK

[75] Inventor: Terry M. Haber, El Toro, Calif.

[73] Assignee: Habley Medical Technology Corporation, Laguna Hills, Calif.

[21] Appl. No.: 232,234

[22] Filed: Aug. 15, 1988

[51] Int. Cl.⁴ ............................................... A61M 5/32
[52] U.S. Cl. ..................................... 604/195; 604/110
[58] Field of Search ............... 604/187, 198, 195, 194, 604/193, 191, 218, 232, 236, 88, 87, 89, 90, 91, 221, 228, 241, 243, 110

[56] References Cited

U.S. PATENT DOCUMENTS

| | | | |
|---|---|---|---|
| 3,923,058 | 12/1975 | Weingarten | 604/191 |
| 3,946,732 | 3/1976 | Hurscham | 604/88 |
| 4,067,333 | 1/1978 | Reinhardt et al. | 604/191 |
| 4,424,057 | 1/1984 | House | 604/88 |

Primary Examiner—John D. Yasko
Attorney, Agent, or Firm—Morland C. Fischer

[57] ABSTRACT

A disposable safety syringe comprising a cylinder which is prefilled with fluid medication, a double ended hypodermic needle cannula, and a cannula lock by which the needle cannula is supported in an axially extended position so that an injection of the fluid medication may be administered. The cannula lock includes a clamp having a pair of oppositely disposed jaws between which the cannula is releasably retained. The fluid medication is carried within the syringe cylinder between piston and plug members, each of which members having respective suction heads which are arranged in spaced, face-to-face alignment with one another. The piston member is advanceable axially and distally through the syringe cylinder whereby to expulse the medication from the cylinder and move the suction head of the piston member into air-tight sealing engagement with the suction head of the plug member at the distal end of the cylinder. The needle cannula penetrates the sealed piston and plug members, such that a retraction of the piston member axially and proximally through the cylinder causes a corresponding withdrawal and relocation of the cannula from the jaws of the cannula lock to the interior of the cylinder, where said cannula is completely surrounded and shielded to prevent a reuse of the cannula and an accidental needle stick.

20 Claims, 2 Drawing Sheets

4,908,022

DISPOSABLE SAFETY SYRINGE HAVING A RETRACTABLE NEEDLE CANNULA AND CANNULA LOCK

BACKGROUND OF THE INVENTION

1. FIELD OF THE INVENTION

This invention relates to a disposable safety syringe having a cannula lock for releasably retaining a needle cannula in an axially extended position at which an injection may be administered, and, more particularly, to engageable piston and plug members which are movable reciprocally through the syringe cylinder to expulse a fluid medication therefrom and to retract the cannula from the cannula lock for relocation to the interior of said cylinder.

2. PRIOR ART

In U.S. patent application Ser. No. 211,366 filed June 24, 1988, which application has been or will be assigned to the assignee of the present application, a combination retractable hypodermic needle cannula and cannula lock is disclosed for a reusable safety syringe. The aforementioned combination cannula and lock is interfaced with a prefilled medication carpule at the interior of the reusable syringe cylinder. By virtue of the foregoing, an efficient locking means was disclosed by which a double ended needle cannula could be either reliably retained in an axially extended position for administering an injection or released from the axially extended position to be retracted within and surrounded by an empty medication carpule.

The invention disclosed in the present patent application is characterized by the same advantages as the invention disclosed in application Ser. No. 211,366. However, this application relates to a disposable safety syringe having a needle cannula which is retractable from an axially extended position for administering an injection to the interior of the syringe cylinder, rather than the interior of a medication carpule, so that the syringe may be discarded with the cannula shielded by and irretrievably located within the cylinder thereof. What is more, the present invention includes the additional advantage of a piston-plug assembly which is movable reciprocally through the syringe cylinder for expulsing the fluid contents thereof via said cannula and for engaging and reliably retaining one end of the cannula so that said cannula may be easily and efficiently retracted into the cylinder.

SUMMARY OF THE INVENTION

In general terms, a disposable safety syringe is disclosed including a hollow cylinder which is prefilled with fluid medication, a retractable double ended hypodermic needle cannula, the proximal end of which communicates with the interior of the cylinder, and a cannula lock which is disposed at the distal end of the cylinder. The cannula lock is provided to releasably retain the cannula in an axially extended position relative to the cylinder so that an injection may be administered at a targeted tissue area of a patient. The cannula lock includes a clamp which has a pair of spaced jaws that are rotatable towards one another and into engagement with the cannula for locking the cannula therebetween. The locking jaws are surrounded by an outer sleeve which is integrally connected to the distal end of the cylinder and is sized to bias the jaws in locking engagement with the cannula. A piston is located at the proximal end of the cylinder and a plug is located adjacent the distal end of the cylinder in spaced, coaxial alignment with the cannula. The fluid medication is carried by the cylinder between the piston and the plug. Each of the piston and plug includes a concave suction head, such that the respective suction heads of the piston and plug are arranged in opposing, face-to-face alignment with one another.

In operation, the piston is moved axially and distally through the syringe cylinder, whereby to cause a corresponding distal movement of the plug to the distal end of said cylinder where the proximal end of the cannula penetrates the plug. The continued distal advancement of the piston towards the plug causes a compression of the fluid medication located between said piston and plug, such that the fluid is expulsed from the cylinder via the cannula. The piston is relocated distally through the cylinder until the respective suction heads of the piston and plug are moved into engagement with one another at the distal end of the cylinder to form an air-tight seal therebetween, whereby the proximal end of the cannula now penetrates both the plug and the piston. The application of a suitable axial and distally directed force to the sealed piston and plug is transferred to the cannula retaining clamp at the distal end of the cylinder, so as to displace said clamp axially and distally relative to the outer sleeve by which the clamp is surrounded. Accordingly, the jaws of the clamp automatically rotate away from one another and out of engagement with the cannula so as to leave said cannula suspended only from the proximal end thereof at the sealed piston and plug.

By applying an axial and proximal pulling force to the sealed piston and plug, the needle cannula is correspondingly withdrawn from the space between the jaws of the clamp to be retracted within the interior of the syringe cylinder. Accordingly, the cannula is completely surrounded and shielded by the cylinder. The syringe may now be discarded with the cannula irretrievably located in the cylinder thereof so as to prevent a reuse of said cannula and an accidental and potentially life threatening needle stick.

DESCRIPTION OF THE PREFERRED EMBODIMENT

Figure 1:
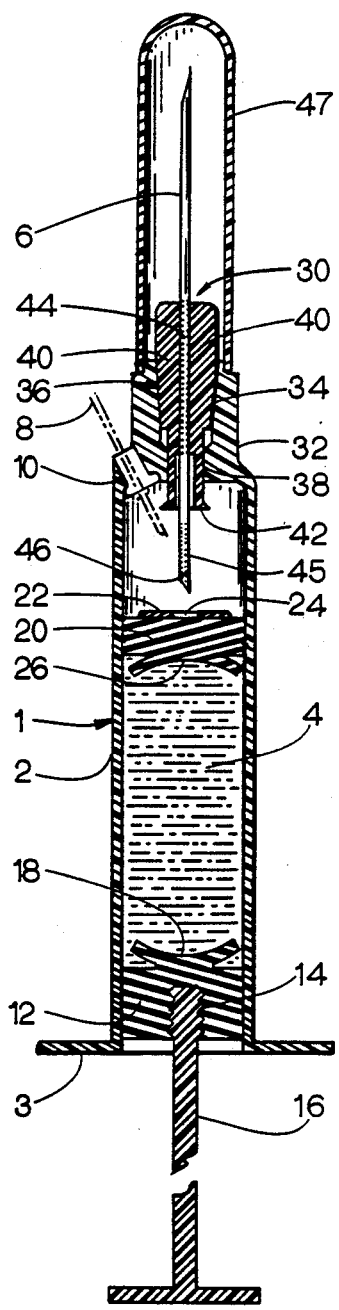
FIG. 1 is a cross section of a disposable safety syringe which forms the present invention in the packaged state with a hypodermic needle cannula retained in an axially extended position.

The disposable safety syringe having a retractable needle cannula and forming the present invention is best described by referring to the drawings, where FIG. 1 shows the safety syringe 1 in the packaged condition suitable for transport and storage prior to use. More particularly, syringe 1 includes a hollow cylinder 2 having an open proximal end and a substantially closed distal end. A flange 3 is formed around the proximal end of cylinder 2 to improve the handling of syringe 1 during use. The cylinder 2 is preferably prefilled with a suitable supply of fluid mediation 4 which is to be expulsed therefrom to a patient by way of a hypodermic needle cannula 6. However, as an alternate embodiment of the invention, an optional needle cannula 8 may communicate with the interior of syringe cylinder 2 via a valve 10. In this manner, it would be possible to fill the cylinder 2 at the time of use with medication from an available external source of supply rather than prefill said cylinder prior to use.

Located within the open proximal end of syringe cylinder 2 is a piston 12. Piston 12 is preferably formed from a relatively dense, resilient, and non-corrosive material, such as rubber, or the like. A screw threaded hole 14 is formed at one end of piston 12. Screw threaded hole 14 is sized to receive and be mated to a detachable screw threaded piston stem 16, whereby to complete a piston assembly comprising piston 12 and stem 16 which, as will soon be described, is adapted to slide axially and reciprocally through syringe cylinder 2 for expulsing the medication 4 therefrom and for retracting the needle cannula thereinto. A concave-shaped suction head 18 extends from the opposite end of piston 12 so as to be movable with said piston through cylinder 2.

A plug member 20 is located within the syringe cylinder 2 and disposed distally therein relative to piston 12. Plug member 20 is preferably made from the same relatively dense material (i.e. rubber, or the like) as is piston 12. Secured at one end of plug 20 is a disk 22. Disk 22 is formed from a hard material, such as metal, that is resistant to penetration by the cannula 6. The disk 22 has a centrally disposed opening 24 formed therein which, in the packaged configuration of FIG. 1, is arranged in spaced, coaxial alignment with respect to the longitudinal axis of cannula 6. Extending from the opposite end of plug 20 is a concave-shaped suction head 26. The suction heads 18 and 26 of piston 12 and plug 20 are initially arranged in spaced, face-to-face alignment with one another with the fluid medication of cylinder 2 carried therebetween. Piston 12 and plug 20 are sized to form fluid-tight seals against the walls of cylinder 2 and thereby prevent the inadvertent escape or contamination of such fluid from the cylinder. As will soon be disclosed in greater detail hereinafter when referring to FIG. 3, the concave suction heads 18 and 26 of piston 12 and plug 20 are adapted to engage one another and form an efficient seal therebetween.

The cannula lock 30 of disposable syringe 1 will now be described. Since the cannula lock 30 is substantially similar to that previously disclosed in patent application Ser. No. 211,366 filed June 24, 1988, only a brief description of said cannula lock will be provided. The cannula lock 30 includes a cylindrical outer sleeve 32 which is integrally connected to and extended outwardly from the distal end of syringe cylinder 2. The outer sleeve 32 has a relatively narrow, tapered bore 34 extending longitudinally through the distal end thereof. The tapered bore 34 is particularly sized to receive and releasably retain a clamp or chuck 36, which is adapted to either lock the needle cannula 6 in an axially extended position or release the needle cannula to be retracted within and completely surrounded by the syringe cylinder 2.

More particularly, the aforementioned clamp or chuck 36 includes a hollow, generally cylindrical base 38 and a pair of parallel aligned jaws 40. The jaws 40 are normally spaced from one another and adapted to rotate relative to the base 38 so as to releasably receive and reliably retain the needle cannula 6 in the space therebetween. The exterior surfaces of jaws 40 have a tapered configuration to match the taper of the distal bore 34 of sleeve 32 so that clamp 36 is adapted to slide axially through the distal bore 34. An annular lip 42 is formed around the bottom of base 38. In the packaged configuration of FIG. 1, lip 42 is spaced proximally from the distal end of cylinder 2 so as to extend slightly therewithin.

Cannula 6 is a conventional double ended, hollow needle cannula of the type commonly associated with many hypodermic syringes. However, cannula 6 includes a high friction, raised or textured medial surface 44 and another high friction, textured surface 45 located adjacent the proximal end thereof. A small aperture 46 is formed in the proximal end of cannula 6 through which fluid from the syringe cylinder 2 is expulsed. A removable needle sheath 47 is also provided to surround cannula 6 during storage and handling to preserve the sterility of the cannula and prevent an accidental needle stick prior to use.

In the assembled relationship of FIG. 1, the needle cannula 6 is positioned within the space between the opposing jaws 40 of the clamp 36. The combination needle cannula 6 and clamp 36 is then located within the distal bore 34 of sleeve 32 so as to secure cannula 6 in an axially extending position for administering an injection. That is, locating the tapered jaws 40 of clamp 36 within the similarly tapered bore 34 of sleeve 32 causes the jaws to rotate towards one another and into frictional engagement with the cannula 6 at the medially disposed textured surface 44 thereof so as to oppose any axial displacement of said cannula relative to clamp 36.

Figure 2:
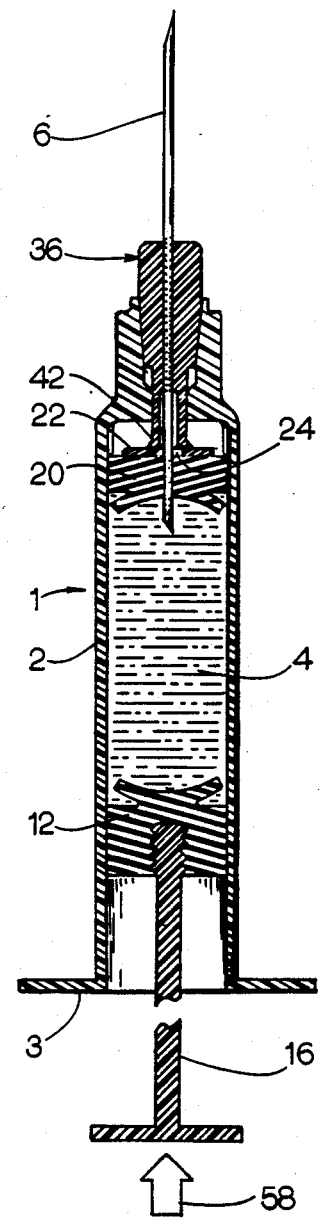
FIG. 2 is a cross section of the safety syringe of FIG. 1 in a pre-injection state.

FIG. 2 of the drawings shows the safety syringe 1 in the pre-injection state with needle sheath 47 removed to expose cannula 6 for administering an injection. That is to say, the health care worker grasps syringe cylinder 2 by locating his fingers below flange 3 and his thumb against piston stem 16. An axial and distally directed force is then applied (in the direction of reference arrow 58) to piston stem 16 to drive piston 12 in a distal direction through cylinder 2. The axial and distally directed force is transferred from piston stem 16 to plug 20 via piston 12 and the continuous column of fluid within cylinder 2. Accordingly, a corresponding axial force is applied to drive plug 20 through cylinder 2 and towards the needle cannula 6, until the proximal end of cannula 6 penetrates the plug 20 at the hole 24 in disk 22. The proximal relocation of plug 20 through syringe cylinder 2 continues until said plug 20 is moved onto contact with the annular lip 42 of clamp 36 below the distal end of cylinder 2.

Figure 3:
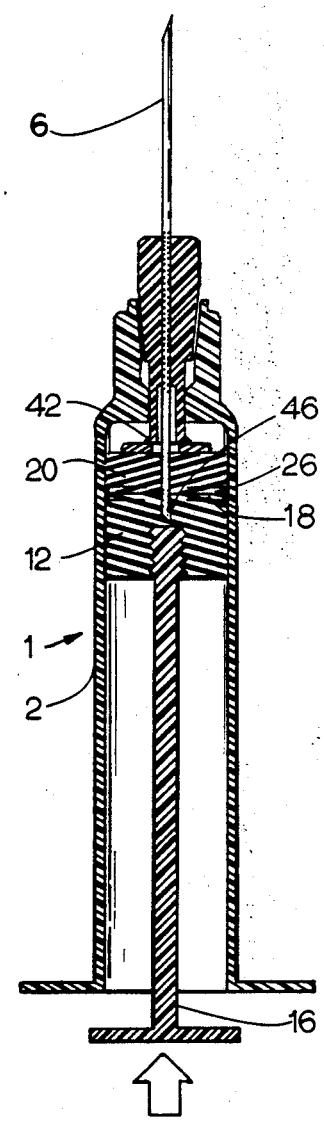
FIG. 3 is a cross section of the safety syringe in an injection state after the fluid contents thereof have been expulsed from the syringe cylinder.

FIG. 3 of the drawings shows the safety syringe 1 in the injection state. More particularly, the distal end of the needle cannula 6 is suitably located at a targeted tissue area of the patient. The health care worker then resumes the application of the axial and distally directed force to piston stem 16 to continue to drive piston 12 through cylinder 2 and towards plug 20. Inasmuch as the distal relocation of plug 20 is blocked by lip 42, the fluid medication within cylinder 2 is compressed between the distally advancing piston 12 and the stationary plug 20. Accordingly, the fluid medication within cylinder 2 is expulsed form the cylinder and delivered to the patient via the aperture 46 and the hollow needle cannula 6. What is more, the respective concave suction heads 18 and 26 of piston 12 and plug 20 are flattened against one another so as to form a planar, air-tight seal and thereby attach the piston 12 and plug member 20 together at the distal end of cylinder 2. At the same time, the proximal end of needle cannula 6 penetrates the piston 12. Therefore, the cannula 6 is firmly anchored to both plug 20 and piston 12 at the distal end of cylinder 2.

Figure 4:
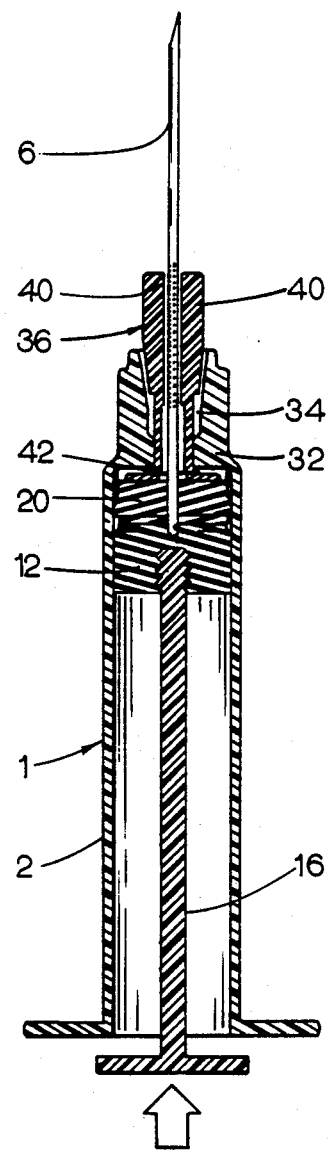
FIG. 4 is a cross section of the syringe cylinder in a post-injection state.

FIG. 4 shows the safety syringe 1 in the post-injection state after the fluid medication has been expulsed from the syringe cylinder 2 and the distal end of cannula 6 has been removed from the tissue of the patient. With the piston 12 and plug 20 sealed together and located at the distal end of cylinder 2 and in contact with the annular lip 42 of clamp 36, a suitable axial and distally directed force is applied to clamp 36 at the inwardly projecting lip 42 thereof by way of the piston stem 16 and the union of piston 12 and plug 20. The axial force applied from piston stem 16 to clamp 36 overcomes the former engagement of clamp 36 by the tapered bore 34 of outer sleeve 32. Hence, the clamp 36 is displaced axially relative to the outer sleeve 32 and, more particularly, distally relative to the distal bore 34 of sleeve 32 whereby to permit the opposing jaws 40 of clamp 36 to rotate away from one another and out of engagement with the needle cannula 6. Therefore, cannula 6 is now supported only at the proximal end thereof by the sealed combination of piston 12 and plug 20 so as to be free for withdrawal from the space between the jaws 40.

Figure 5:
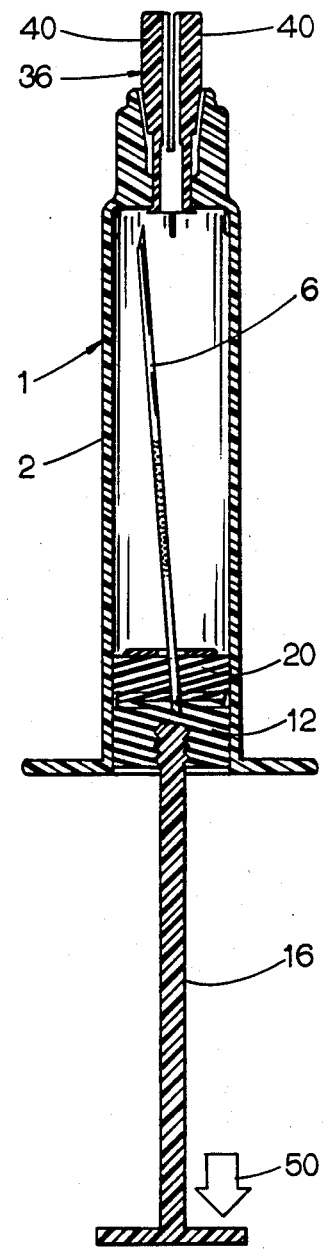
FIG. 5 is a cross section of the safety syringe in a retracted state with the needle cannula retracted within and completely surrounded by the syringe cylinder.

FIG. 5 of the drawings shows the safety syringe 1 in the retracted state with needle cannula 6 located within and completely surrounded by the empty syringe cylinder 2. That is, the health care worker applies an axial and proximal pulling force (in the direction of reference arrow 50) to the piston stem 16 to relocate the needle cannula 6 from the axially extended position, at which the injection was administered, to a relatively proximal position within cylinder 2. The pulling force applied to piston stem 16 is transferred to the cannula 6 by way of the sealed piston 12 and plug 20. Accordingly, the cannula 6 is withdrawn from the space between the jaws 40 of clamp 36 to be retracted within the cylinder 2. By virtue of the foregoing, the cannula 6 is safely shielded by the cylinder, whereby to prevent a reuse of the cannula and avoid an accidental and possibly life threatening needle stick.

Thereafter, the piston stem 16 may be detached from the piston 12 and discarded. The syringe 1 may also be discarded with the cannula 6 irretrievably located and shielded at the interior of the cylinder 2. Also by virtue of the present invention, the attachment of cannula 6 to the relatively dense material of piston 12 and plug 20 will cause said cannula to be automatically canted when said cannula is retracted into the cylinder. In this manner, it would be possible to prevent the return of the canted cannula to the axially extended position (of FIG. 3) in the event that the piston stem and the cannula connected thereto were to be inadvertently moved axially and distally through the cylinder.

As a further advantage of the present invention, it may be noted that in the packaged configuration of FIG. 1, the axially spaced piston 12 and plug 20 completely isolate the fluid medication 4 from the needle cannula 6. Accordingly, the possibility of a corrosive reaction between the cannula and the fluid will be avoided. Moreover, by isolating the fluid 4 in the manner disclosed, there will be less chance of contamination. Thus, the syringe 1 of the present invention provides many of the same advantages as would be provided by a syringe in which a medication filled carpule is received, but the added cost and storage inconveniences that are associated with such carpules are eliminated.

It will be apparent that while a preferred embodiment of the invention has been shown and described, various modifications and changes may be made without departing from the true spirit and scope of the invention. For example, the disclosed safety syringe has particular application as a dental syringe. However, it is to be understood and this use is for purposes of example only, and the advantages of this invention and the teachings of this application are applicable to other types of syringes, as well.

Having thus set forth a preferred embodiment of the invention, what is claimed is:

1. A syringe comprising:
   a hollow cylinder having proximal and distal ends and containing a supply of fluid to be administered to a patient;
   a double ended hypodermic needle cannula, a first end of said cannula extending into the interior of said cylinder, and the opposite end of said cannula extending outwardly from said cylinder for administering an injection;
   means for supporting said cannula at the distal end of said cylinder;
   a plug located at a relatively distal position within said cylinder so as to be separated from the first end of said cannula;
   a piston located at a relatively proximal position within said cylinder in spaced axial alignment with said plug, whereby the fluid of said cylinder is received in the space between said plug and piston, said piston being movable distally through said cylinder and towards said plug for causing a corresponding distal movement of said plug, such that the first end of said cannula penetrates said plug and communicates with the fluid between said plug and said piston, and
   sealing means to form an air-tight seal between said piston and said plug to thereby fixedly attach said piston to said plug after said piston has been moved distally through said cylinder and into contact with said plug.

2. The syringe recited in claim 1, wherein said sealing means for attaching said piston to said plug is a concave-shaped suction head extending from at least one of said piston or plug and adapted to form an air-tight seal with the other of said piston or plug when said piston is moved into contact with said plug.

3. The syringe recited in claim 1, wherein said sealing means for attaching said piston to said plug includes respective suction surfaces extending from each of said piston and plug and arranged in face-to-face alignment with one another so as to form an air-tight seal therebetween when said piston is moved into contact with said plug.

4. The syringe recited in claim 5, wherein said respective suction surfaces are each concave-shaped suction heads.

5. The syringe recited in claim 1, including means by which to move said piston proximally through said cylinder for correspondingly relocating said plug to a relatively proximal position within said cylinder and thereby withdrawing said needle cannula from said cannula supporting means such that said cannula is retracted within and completely surrounded by said cylinder.

6. The syringe recited in claim 5, wherein said means for moving said piston proximally through said cylinder for relocating said plug is a piston stem.

7. The syringe recited in claim 5, wherein said means for supporting said cannula includes means for releasing said cannula from the distal end of said cylinder for retraction therewithin when said piston is moved proximally through said cylinder and said plug is correspondingly relocated.

8. The syringe recited in claim 7, wherein said cannula supporting means for releasing said cannula from the distal end of said cylinder comprises:
 a set of normally spaced jaws that are movable towards one another for engaging said cannula therebetween;
 an outer sleeve surrounding said jaws for moving said jaws towards one another and into engagement with said cannula; and
 means to displace said jaws axially relative to said outer sleeve so that said jaws are free to move away from one another and out of engagement with said cannula to permit said cannula to be removed from said jaws.

9. The syringe recited in claim 8, wherein the means to displace said jaws relative to said outer sleeve is the continued distal movement of said piston and said plug through said cylinder and into contact with said cannula supporting means at the distal end of said cylinder after said piston and said plug have been connected to one another.

10. A disposable safety syringe having a retractable needle cannula and comprising:
 a hollow cylinder having proximal and distal ends and containing a supply of fluid to be administered to a patient;
 a double ended hypodermic needle cannula, a first end of said cannula extending into the interior of said cylinder, and the opposite end of said cannula extending outwardly from said cylinder for administering an injection;
 means for releasably retaining said cannula at the distal end of said cylinder;
 a plug located within said cylinder to be positioned at the distal end thereof, such that the first end of said cannula penetrates said plug;
 a piston located at the proximal end of said cylinder in spaced axial alignment with said plug, whereby the fluid in said cylinder is received in the space between said piston and said plug; and
 means to move said piston distally through said cylinder and towards said plug to expulse the fluid from said cylinder via said cannula and to connect said piston to said plug, and to move said piston proximally through said cylinder to relocate said plug to a relatively proximal position within said cylinder and correspondingly withdraw said cannula from said retaining means for retraction completely within said cylinder.

11. The syringe recited in claim 10, further comprising respective suction surfaces extending from each of said piston and plug and arranged in face-to-face alignment with one another to thereby form an air-tight seal therebetween for connecting said piston and said plug together when said piston is moved distally through said cylinder so as to contact said plug.

12. The syringe recited in claim 11, wherein said respective suction surfaces are concave-shaped suction heads.

13. The syringe recited in claim 10, further comprising at least one suction surface formed at one of said piston or said plug and aligned with the other of said piston or said plug to form an air-tight seal therewith for connecting said piston to said plug when said piston is moved distally through said cylinder and into contact with said plug.

14. The syringe recited in claim 10, wherein the means for moving said piston distally and proximally through said cylinder is a piston stem.

15. The syringe recited in claim 10, wherein said means for releasably retaining said cannula at the distal end of said cylinder comprises:
 a set of normally spaced jaws that are movable towards one another for engaging said cannula therebetween;
 an outer sleeve surrounding said jaws for moving said jaws towards one another and into engagement with said cannula; and
 means to displace said jaws axially relative to said outer sleeve so that said jaws are free to move away from one another and out of engagement with said cannula to permit said cannula to be removed from said jaws.

16. The syringe recited in claim 15, wherein the means to displace said jaws relative to said outer sleeve is the continued distal movement of said plug through said cylinder and into contact with said jaws after said piston and said plug have been connected to one another.

17. A safety syringe having a retractable needle cannula and comprising:
 a hollow cylinder having proximal and distal ends and containing a supply of fluid to be administered to a patient;
 a double ended hypodermic needle cannula, a first end of said cannula extending into the interior of said cylinder, and the opposite end of said cannula extending outwardly from said cylinder for administering an injection;
 means for removably retaining said cannula at the distal end of said cylinder;
 a plug located at the distal end of said cylinder;
 a piston located at the proximal end of said cylinder in spaced axial alignment with said plug, whereby the fluid in said cylinder is received in the space between said piston and said plug; and
 means to move said piston axially and reciprocally through said cylinder, such that a distal movement of said piston through said cylinder and towards said plug expulses the fluid from said cylinder via said cannula and causes said plug and said piston to be penetrated by the first end of said cannula, and a proximal movement of said piston through said cylinder removes said cannula from said retaining means and relocates said cannula and the plug penetrated thereby towards the proximal end of said cylinder such that said cannula is withdrawn completely within said cylinder.

18. The syringe recited in claim 17, further comprising means by which to connect said piston to said plug when said piston is moved distally through said cylinder and towards said plug.

19. The syringe recited in claim 18, wherein said means to connect includes a suction surface formed on at least one of said piston or said plug to form an air-tight seal with the other of said piston or said plug.

20. The syringe recited in claim 19, wherein said suction surface includes a concave shaped suction head.

* * * * *